United States Patent
Yamada et al.

(10) Patent No.: US 11,828,698 B2
(45) Date of Patent: Nov. 28, 2023

(54) AMBIENT-HYDROGEN-LEVEL ASSESSMENT METHOD AND WHITE-STRUCTURE-DAMAGE-LIKELIHOOD PREDICTION METHOD

(71) Applicant: NSK Ltd., Tokyo (JP)

(72) Inventors: Hiroki Yamada, Fujisawa (JP); Atsushi Imai, Fujisawa (JP); Hideyuki Uyama, Fujisawa (JP)

(73) Assignee: NSK Ltd., Tokyo (JP)

( * ) Notice: Subject to any disclaimer, the term of this patent is extended or adjusted under 35 U.S.C. 154(b) by 264 days.

(21) Appl. No.: 17/272,423

(22) PCT Filed: Oct. 31, 2019

(86) PCT No.: PCT/JP2019/042833
§ 371 (c)(1),
(2) Date: Mar. 1, 2021

(87) PCT Pub. No.: WO2020/110593
PCT Pub. Date: Jun. 4, 2020

(65) Prior Publication Data
US 2021/0318227 A1  Oct. 14, 2021

(30) Foreign Application Priority Data

Nov. 30, 2018  (JP) ................. 2018-224838

(51) Int. Cl.
*G01N 17/00* (2006.01)
*F16C 19/52* (2006.01)
*G01M 13/04* (2019.01)

(52) U.S. Cl.
CPC ........... *G01N 17/002* (2013.01); *F16C 19/52* (2013.01); *G01M 13/04* (2013.01); *G01N 17/006* (2013.01)

(58) Field of Classification Search
CPC ............... G01N 17/002; G01N 17/006; G01N 33/2025; G01M 13/04; F16C 19/52
See application file for complete search history.

(56) References Cited

U.S. PATENT DOCUMENTS

2004/0079310 A1* 4/2004 Suzuki .................... F16C 13/02
  123/90.41
2004/0170348 A1  9/2004 Okugami et al.
2014/0157874 A1* 6/2014 Strandell ............ G01N 15/0826
  73/38

FOREIGN PATENT DOCUMENTS

EP  1 676 932 A1  7/2006
JP  11-94704 A  4/1999
(Continued)

OTHER PUBLICATIONS

Evans, M. H., et al., "Effect of hydrogen on butterfly and white etching crack (WEC) formation under rolling contact fatigue (RCF)", Wear, Mar. 15, 2013, pp. 226-241, vol. 306, No. 1, XP028756684. (16 pages).

(Continued)

*Primary Examiner* — Manuel L Barbee
(74) *Attorney, Agent, or Firm* — Crowell & Moring LLP

(57) ABSTRACT

Provided are a method for assessing hydrogen environment severity of a rolling device during operation and a method for predicting likelihood that white structure damage occurs to the rolling device as a result of operation. A hydrogen environment severity assessment method is a method for assessing, among operating conditions of a rolling device including two rolling members coming into rolling contact with each other and having at least one of the two rolling members being a steel rolling member, hydrogen environment severity, the hydrogen environment severity being an index representing magnitude of influence exerted by hydrogen. The hydrogen environment severity assessment method (Continued)

includes a measurement step of measuring the amount of room temperature non-diffusible hydrogen contained in a rolling fatigue region, the rolling fatigue region being a region where rolling fatigue has been produced by rolling contact, within the steel rolling member of the rolling device operated under the operating conditions and an assessment step of assessing the hydrogen environment severity, based on a measurement result in the measurement step.

10 Claims, 2 Drawing Sheets

(56) References Cited

FOREIGN PATENT DOCUMENTS

| | | |
|---|---|---|
| JP | 2004-278782 A | 10/2004 |
| JP | 2009-19639 A | 1/2009 |
| JP | 6072504 B2 | 2/2017 |
| JP | 2017-122633 A | 7/2017 |
| JP | 2019-35756 A | 3/2019 |

OTHER PUBLICATIONS

Supplementary European Search Report issued in European Application No. 19890674.5 dated Aug. 10, 2021 (seven (7) pages).
International Preliminary Report on Patentability (PCT/IB/338 & PCT/IB/373) issued in PCT Application No. PCT/JP2019/042833 dated Jun. 10, 2021, Including English translation of document C2 (Japanese-language Written Opinion (PCT/ISA/237), filed on Mar. 1, 2021) (seven (7) pages).
International Search Report (PCT/ISA/210) issued in PCT Application No. PCT/JP2019/042833 dated Dec. 24, 2019 with English translation (five (5) pages).
Japanese-language Written Opinion (PCT/ISA/237) issued in PCT Application No. PCT/JP2019/042833 dated Dec. 24, 2019 (five (5) pages).
Matsunaga et al., "Effect of hydrogen on shear-mode fatigue crack growth in rolling contact fatigue of a bearing steel," Proceedings of the Materials & Mechanics Conference, Oct. 10, 2013, pp. 1-2, No. 13-8, Rombunno. OS2107 with English abstract (two (2) pages).

* cited by examiner

AMBIENT-HYDROGEN-LEVEL ASSESSMENT METHOD AND WHITE-STRUCTURE-DAMAGE-LIKELIHOOD PREDICTION METHOD

TECHNICAL FIELD

The present invention relates to a hydrogen environment severity assessment method and a white structure damage likelihood prediction method.

BACKGROUND ART

When hydrogen penetrates into steel that forms rolling members of a rolling device, metal structure of steel sometimes changes due to interaction between shear stress exerted on the inside of steel caused by rolling contact and hydrogen. This change in metal structure is a phenomenon in which martensite that is matrix structure of steel transforms into fine ferrite grains. Since, when etching is performed and a structurally changed part is observed, the structurally changed part looks white, metal structure that has changed due to penetration of hydrogen is referred to as "white structure". Since, when white structure occurs to steel, fatigue crack starts from an interface between a structurally changed part and a normal part (structurally non-changed part) and flaking occurs, there is a possibility that a rolling fatigue life of a rolling member substantially deteriorates. Hereinafter, flaking accompanied by structural change into white structure as described above is sometimes referred to as "white structure flaking". Damage caused by white structure (including white structure flaking) is sometimes referred to as "white structure damage".

Quantifying the amount of room temperature diffusible hydrogen among hydrogen having penetrated into a rolling member during operation of a rolling device enables a degree of severity of a hydrogen environment (hereinafter, sometimes referred to as "hydrogen environment severity") of the rolling device during operation to be assessed or a life affected by white structure flaking to be predicted (see, for example, PTL 1).

However, in the case of a rolling device used in an actual machine (for example, an alternator for vehicle), accurate quantification of the amount of room temperature diffusible hydrogen has been difficult because room temperature diffusible hydrogen is sometimes discharged from the rolling member before measurement even if the amount of room temperature diffusible hydrogen contained in the rolling member is to be quantified. Therefore, it has been difficult to assess hydrogen environment severity of a rolling device when the rolling device is used in an actual machine or to predict likelihood that white structure damage, such as white structure flaking, occurs to a rolling device used in an actual machine.

In addition, it has not been easy to measure concentration of hydrogen gas in an atmosphere in which the rolling device is placed during operation and likelihood of generation of hydrogen due to decomposition of a lubricant used for the rolling device.

CITATION LIST

Patent Literature

PTL 1: JP 6072504 B

SUMMARY OF INVENTION

Technical Problem

A problem to be solved by the present invention is to provide a method for assessing hydrogen environment severity of a rolling device during operation and a method for predicting likelihood that white structure damage occurs to the rolling device as a result of operation.

Solution to Problem

A hydrogen environment severity assessment method according to one aspect of the present invention is a method for assessing, among operating conditions of a rolling device including two rolling members coming into rolling contact with each other and having at least one of the two rolling members being a steel rolling member, hydrogen environment severity, the hydrogen environment severity being an index representing the magnitude of influence exerted by hydrogen. The hydrogen environment severity assessment method according to the one aspect of the present invention includes a measurement step of measuring the amount of room temperature non-diffusible hydrogen contained in a rolling fatigue region, the rolling fatigue region being a region where rolling fatigue has been produced by rolling contact, within the steel rolling member of the rolling device operated under the operating conditions and an assessment step of assessing the hydrogen environment severity, based on a measurement result in the measurement step.

A white structure damage likelihood prediction method according to another aspect of the present invention is a method for, using the hydrogen environment severity assessment method according to the one aspect, predicting likelihood that white structure damage occurs to the steel rolling members during operation of a rolling device.

In the white structure damage likelihood prediction method according to the another aspect of the present invention, first, a rolling device of the same type as a rolling device for which likelihood that white structure damage occurs is to be predicted is prepared as a rolling device for database generation, and the rolling device for database generation is operated under each of a plurality of operating conditions in each of which at least one of the magnitude and the number of repetitions of stress exerted on a rolling fatigue region of a steel rolling member due to rolling contact, temperature during operation, and a hydrogen environment of the rolling device for database generation during operation is different from the other conditions. Every time the operation is finished, the amount of room temperature non-diffusible hydrogen contained in the rolling fatigue region of the steel rolling member of the rolling device for database generation is measured and an increase rate of the amount of room temperature non-diffusible hydrogen contained in the rolling fatigue region of the steel rolling member of the rolling device for database generation is calculated and, in conjunction therewith, whether or not white structure damage has occurred to the steel rolling member of the rolling device for database generation is confirmed, and a database in which the calculation results and confirmation results classified for each of the plurality of operating conditions are stored is generated in advance.

Next, the calculation result and the confirmation result in a case where all of the magnitude and the number of repetitions of stress exerted on a rolling fatigue region of a steel rolling member due to rolling contact and temperature during operation are the same as operating conditions of a rolling device for which likelihood that the white structure damage occurs is to be predicted are acquired or estimated from the database, and, using the acquired or estimated calculation result and confirmation result, an increase rate of the amount of room temperature non-diffusible hydrogen serving as a critical value at which the white structure damage begins to occur is calculated.

In the assessment step, by comparing an increase rate of the amount of room temperature non-diffusible hydrogen calculated with respect to a rolling device for which likelihood that the white structure damage occurs is to be predicted with the critical value, likelihood that white structure damage occurs to the steel rolling member during operation of the rolling device for which likelihood that the white structure damage occurs is to be predicted is predicted.

Advantageous Effects of Invention

The present invention enables hydrogen environment severity of a rolling device during operation to be assessed. The present invention also enables likelihood that white structure damage occurs to the rolling device as a result of operation to be predicted.

DESCRIPTION OF EMBODIMENTS

Figure 1:
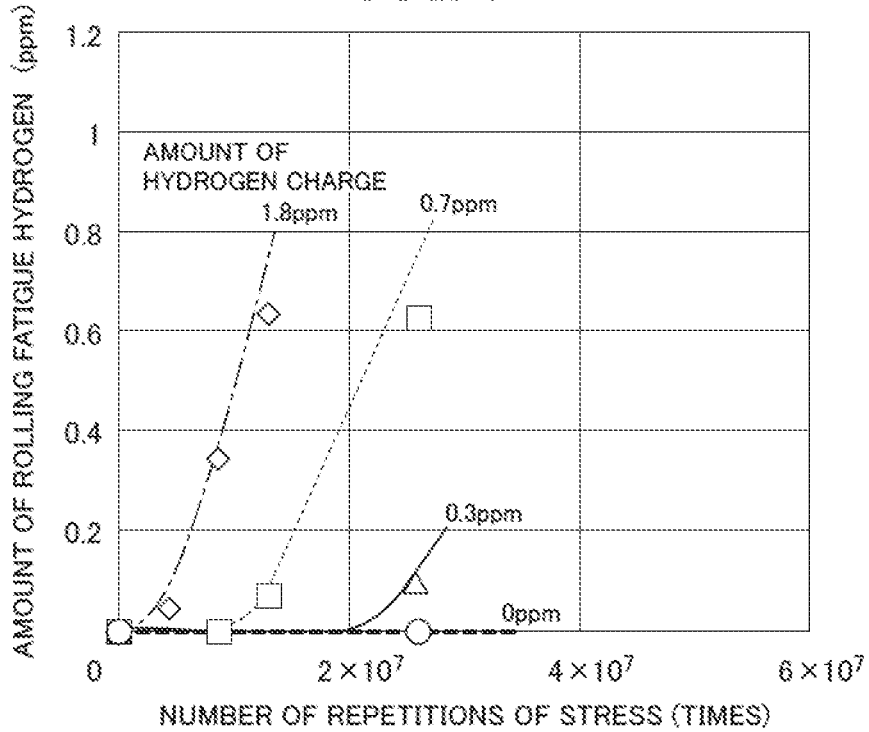
FIG. 1 is a graph illustrative of a relationship between the amount of hydrogen charge to steel and an increase rate of the amount of rolling fatigue hydrogen.

First, definitions of terms used in the description of the present invention will be collectively described.

"White structure flaking" means flaking that occurs to steel rolling members in a rolling device, accompanied by structural change to white structure, as described afore.

"White structure damage" means damage that occurs to the steel rolling members in the rolling device, caused by white structure, as described afore and includes white structure flaking.

"Hydrogen environment" means an environment relating to hydrogen among various types of environments in which the rolling device is placed during operation (such as, the magnitude of stress exerted on the steel rolling members (surface pressure), the number of repetitions of stress exerted on the steel rolling members, an atmosphere around the rolling device, and temperature). For example, an atmosphere in which the rolling device is placed during operation and a lubricant, such as lubricating oil, used for the rolling device are included in the "hydrogen environment". The reason why a lubricant, such as lubricating oil, is included in the "hydrogen environment" is that such a lubricant is decomposed and generates hydrogen during operation of the rolling device.

"Hydrogen environment severity" means a degree of severity of the hydrogen environment of the rolling device during operation and is an index representing the magnitude of influence exerted on the steel rolling members by hydrogen therearound. For example, concentration of hydrogen gas in an atmosphere in which the rolling device is placed during operation and likelihood of hydrogen being generated due to decomposition of a lubricant used for the rolling device are included in the "hydrogen environment severity".

"White structure damage likelihood" means the magnitude of likelihood that white structure damage occurs to the steel rolling members during operation of the rolling device. The white structure damage likelihood is determined based on hydrogen environment severity (such as, concentration of hydrogen gas in an atmosphere around the rolling device and the type of lubricant used for the rolling device), the magnitude of stress exerted on the steel rolling members (surface pressure), the number of repetitions of stress exerted on the steel rolling members, the type of steel that forms the steel rolling members, surface roughness of the steel rolling members, temperature, and the like.

"Room temperature diffusible hydrogen" means hydrogen that is comparatively weakly trapped in steel and can comparatively freely move within the steel rolling members. The room temperature diffusible hydrogen can be discharged from the steel rolling members to the outside at room temperature over time.

"Room temperature non-diffusible hydrogen" means hydrogen that is comparatively strongly trapped in steel and cannot freely move within the steel rolling members. The room temperature non-diffusible hydrogen is not discharged from the steel rolling members to the outside at room temperature.

The "room temperature" is temperature stipulated in JIS Z8703 and is specifically a temperature in a range of 5° C. or more and 35° C. or less.

A "rolling device" means a device that includes two rolling members that come into rolling contact with each other, and, for example, rolling bearings, ball screws, linear guide devices, linear bearings, and the like are included in the rolling devices.

"Rolling members" are components constituting a rolling device and mean members that come into rolling contact with each other. Specifically, rolling members mean an inner ring, an outer ring, and rolling elements in the case where the rolling device is a rolling bearing, a screw shaft, a nut, and rolling elements in the case of a ball screw, a guide rail, a slider, and rolling elements in the case of a linear guide device, or a shaft, an outer cylinder, and rolling elements in the case of a linear bearing.

Next, an embodiment of the present invention will be described. New knowledge on steel and hydrogen acquired as a result of earnest examination made by the inventors will be described in detail below.

In the research on hydrogen embrittlement that causes a reduction in strength of steel, it is a general consensus that room temperature diffusible hydrogen, which can move in steel at room temperature, is harmful with regard to hydrogen embrittlement and room temperature non-diffusible hydrogen, which does not move in steel at room temperature, is harmless with regard to hydrogen embrittlement. Thus, originally, in order to quantify hydrogen environment severity of a rolling device, it is preferable to measure the amount of room temperature diffusible hydrogen, which is likely to cause white structure damage, such as white structure flaking, to occur to steel rolling members.

However, since temperature of steel rolling members in a rolling device in operation is generally higher than room temperature, room temperature diffusible hydrogen is rapidly discharged to the outside from the steel rolling members in the rolling device after operation, as a result of which it has been difficult to accurately measure the amount of room temperature diffusible hydrogen.

On the other hand, it has been known that, in steel rolling members in a rolling device to which white structure damage, such as white structure flaking, has occurred due to rolling fatigue, the amount of room temperature non-diffusible hydrogen has increased. It has also been known that, even in steel rolling members in a rolling device that has not been used, room temperature non-diffusible hydrogen that penetrated into the steel rolling members at the time of heat treatment or the like exists.

Accordingly, the inventors have examined methods for quantifying hydrogen environment severity of a hydrogen environment in which a rolling device is used, using room temperature non-diffusible hydrogen, which is measurable, in place of room temperature diffusible hydrogen, which is difficult to measure although correlated with hydrogen environment severity. As a result of the examination, the inventors have found that an increase rate of the amount of room temperature non-diffusible hydrogen contained in steel rolling members in a rolling device is correlated with hydrogen environment severity, which has led to the completion of the present invention. The examination by the inventors will be described in detail below.

First, an example of a process in which white structure flaking occurs will be described. When a tribochemical reaction occurs during operation of a rolling device, lubricant, such as lubricating oil, is decomposed and hydrogen is generated. Generated hydrogen penetrates into steel from a raceway surface of a steel rolling member in the form of hydrogen atoms. It is conjectured that penetrating hydrogen diffuses in steel as room temperature diffusible hydrogen, metal fatigue is accelerated because of hydrogen embrittlement in a region where shear stress is high, causing a structural change to occur, white structure is formed as a result of the structural change, and flaking finally occurs, accompanied by cracking, chipping, and breaking.

Since, when the operation of the rolling device is suspended, penetration of hydrogen from the raceway surface of the steel rolling member is stopped, only discharge of hydrogen from the steel rolling member to the outside continues, as a result of which all room temperature diffusible hydrogen is discharged from the steel rolling member in a comparatively short period of time. As such, only simply measuring the amount of hydrogen contained in the steel rolling members of the rolling device after operation has not enabled the quantification of the amount of room temperature diffusible hydrogen having existed in the steel rolling members of the rolling device in operation.

However, regarding the rolling fatigue, new trapping sites are generated due to fatigue during the above-described rolling fatigue process. Since such trapping sites newly generated during the rolling fatigue process have high trapping energy, a portion of room temperature diffusible hydrogen that have approached the trapping sites becomes room temperature non-diffusible hydrogen and stays in the steel rolling members without being discharged even after operation. The room temperature non-diffusible hydrogen that has increased between before and after operation is hereinafter sometimes referred to as "rolling fatigue hydrogen".

Since the rolling fatigue hydrogen is room temperature non-diffusible hydrogen, it is considered that the rolling fatigue hydrogen is not a direct cause for hydrogen embrittlement. However, considering that there exists some relationship between the amount of room temperature diffusible hydrogen, which is conjectured to be a cause for the above-described white structure formation, and the amount of rolling fatigue hydrogen, the inventors have performed the following investigation.

A rolling life test was performed using a deep-groove ball bearing having bearing designation 6206. The inner ring and the outer ring are made of SUJ2, and the balls are made of SUJ2 on which carbonitriding treatment was performed. Test conditions are as follows: a ratio of dynamic equivalent load P to basic dynamic load rating C is 0.46; rotational speed is 3000 $min^{-1}$; and temperature is 110° C. Performing the rolling life tests while changing the type of lubricating oil to various types resulted in knowledge described below.

The amount of rolling fatigue hydrogen increased as the test duration of the rolling life test increased.

The increase rate of the amount of rolling fatigue hydrogen and the test duration until white structure flaking occurs vary depending on the type of lubricating oil.

The higher the increase rate of the amount of rolling fatigue hydrogen is, the shorter the test duration until white structure flaking occurs (white structure flaking life) is.

Although, even when the increase rate of the amount of rolling fatigue hydrogen is low, the amount of rolling fatigue hydrogen increases when the test is performed for a long period of time, there is a case where white structure flaking does not occur.

The above-described knowledge reveals that there is no correlativity between the absolute amount of rolling fatigue hydrogen and the white structure flaking life. As such, simply measuring the amount of rolling fatigue hydrogen (room temperature non-diffusible hydrogen) in steel has not enabled quantification of severity of a hydrogen environment during operation. It is conjectured that this is because, since the rolling fatigue hydrogen is room temperature non-diffusible hydrogen, the rolling fatigue hydrogen is hydrogen that does not influence hydrogen embrittlement.

However, it is revealed that there is correlativity between, instead of the absolute amount of rolling fatigue hydrogen, the increase rate of rolling fatigue hydrogen and the white structure flaking life. It is conjectured that, since, when the amount of room temperature diffusible hydrogen having penetrated into steel is large, the room temperature diffusible hydrogen is likely to be trapped in trapping sites newly generated during a rolling fatigue process, the increase rate of rolling fatigue hydrogen accelerates. In other words, the increase rate of the amount of rolling fatigue hydrogen can be used as an alternative index of the amount of room temperature diffusible hydrogen during operation of the rolling device.

Factors influencing increase in the amount of rolling fatigue hydrogen are considered to mainly include the following three items:

(1) operating time of a rolling device, that is, the number of times that stress is exerted on a rolling fatigue region of a steel rolling member due to rolling contact (the number of repetitions of stress);

(2) the magnitude of stress exerted on the rolling fatigue region of the steel rolling member due to rolling contact (surface pressure); and (3) the amount of room temperature diffusible hydrogen of the rolling device during operation.

Further, it is considered that other factors, such as temperature, also influence increase in the amount of rolling fatigue hydrogen.

A result of a test verifying the above-described item (1) is illustrated in a graph in FIG. 1. This test is a test in which hydrogen charge is performed on a circular plate-shaped test piece made of steel and hydrogen is thereby artificially made to penetrate into the test piece and, subsequently, a rolling life test is performed. The hydrogen charge was performed by dipping the circular plate-shaped test piece in an ammonium thiocyanate aqueous solution at a temperature of 50° C. for 24 hours. By varying concentration of the ammonium thiocyanate aqueous solution, the amount of hydrogen charge was adjusted to values as illustrated in the graph (0 to 1.8 ppm).

Details and conditions of the rolling life test are as follows. A thrust ball bearing was produced by setting the raceway ring of a thrust ball bearing having bearing designation 51305 as a rotating ring and the above-described circular plate-shaped test piece as a fixed ring and arranging six rolling elements (steel balls having a diameter of 3/8 inches) and a holder made of steel between both rings. A thrust type rolling life test was performed by, while applying an axial load, rotating the thrust ball bearing in lubricating oil. The lubricating oil used is a lubricating oil the ISO viscosity grade of which is ISO VG68. After the test had ended, the amount of room temperature non-diffusible hydrogen contained in the circular plate-shaped test piece was measured.

The amount of hydrogen charge into the circular plate-shaped test piece is equivalent to the amount of room temperature diffusible hydrogen of the rolling device during operation. The amount of rolling fatigue hydrogen represented by the ordinate of the graph in FIG. 1 is the amount of room temperature non-diffusible hydrogen that has increased between before and after the test.

From the curves representing the amount of rolling fatigue hydrogen drawn in the graph in FIG. 1, it is revealed that the amount of rolling fatigue hydrogen contained in the circular plate-shaped test piece increases as the number of repetitions of stress increases.

From the graph in FIG. 1, it is also revealed that the larger the amount of hydrogen charge, that is, the amount of room temperature diffusible hydrogen at the initial stage of the rolling life test, is, the higher the increase rate of the amount of rolling fatigue hydrogen (the slope of a curve representing the amount of rolling fatigue hydrogen) is. Since the amount of room temperature diffusible hydrogen at the initial stage of the rolling life test indicates a degree of severity of hydrogen environment (hydrogen environment severity) in this test, the graph in FIG. 1 indicates that the severer the hydrogen environment is, the higher the increase rate of the amount of rolling fatigue hydrogen becomes.

Figure 2:
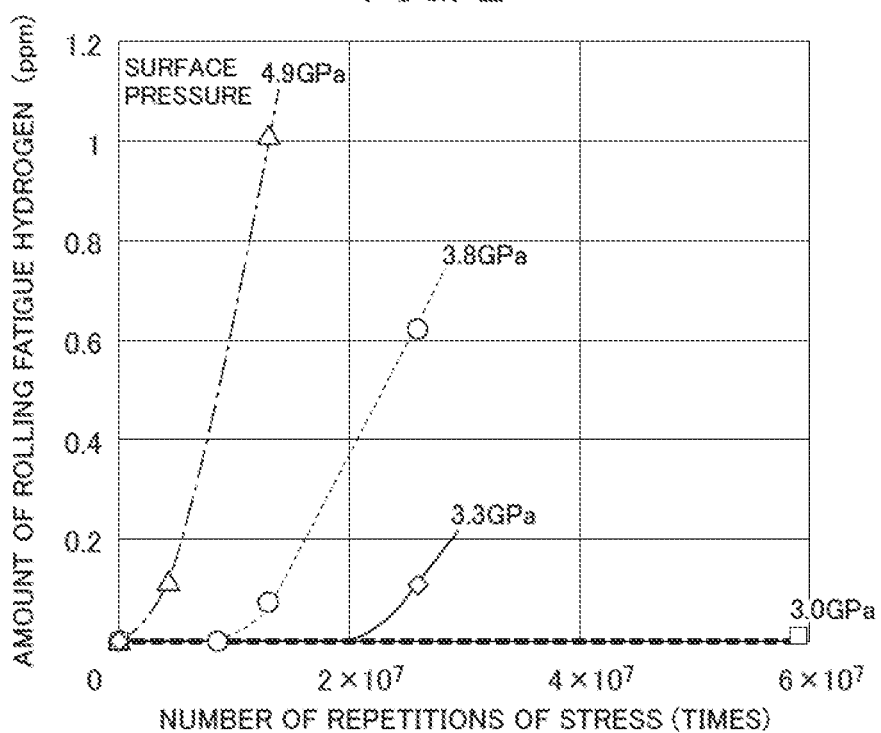
FIG. 2 is a graph illustrative of a relationship between surface pressure and the increase rate of the amount of rolling fatigue hydrogen in a rolling fatigue life test.

Next, a result of a test verifying the above-described item (2) is illustrated in a graph in FIG. 2. Although this test is substantially the same test as the test for verification of the above-described item (1), the amounts of hydrogen charge into a circular plate-shaped test piece are unified to 0.7 ppm and surface pressure is set at values as illustrated in the graph in FIG. 2 (3.0 to 4.9 GPa) in this test.

From the graph in FIG. 2, it is revealed that the higher the surface pressure is, the higher the increase rate of the amount of rolling fatigue hydrogen (the slope of a curve representing the amount of rolling fatigue hydrogen) is. It is conjectured that this is because, since the higher the surface pressure is, the larger stress volume (a region subjected to fatigue due to shear stress) inside a circular plate-shaped test piece becomes, the volume of a region in which a structural change to white structure occurs has increased and the increase rate of the amount of rolling fatigue hydrogen has risen.

It is also conjectured that, since the higher the surface pressure is, the higher shear stress inside a circular plate-shaped test piece becomes, fatigue accelerates and a structural change to white structure occurs in a short period of time.

From these results, it has been found that the amount of rolling fatigue hydrogen (an increased amount of room temperature non-diffusible hydrogen between before and after test) is expressed by a function of the degree of severity of hydrogen environment, the number of repetitions of stress, and the surface pressure. In other words, the degree of severity of hydrogen environment (hydrogen environment severity) can be expressed by a function of the amount of rolling fatigue hydrogen, the number of repetitions of stress, and the surface pressure.

From the above-described verification results, the inventors have found a method for assessing, among operating conditions for a rolling device that includes two rolling members that come into rolling contact with each other and in which at least one of the two rolling members is a steel rolling member, hydrogen environment severity that is an index representing the magnitude of influence exerted by hydrogen. In other words, the hydrogen environment severity assessment method of the present embodiment includes a measurement step of measuring the amount of room temperature non-diffusible hydrogen contained in a rolling fatigue region that is a region where rolling fatigue has been produced by rolling contact within a steel rolling member of a rolling device that has been operated under the above-described operating conditions and an assessment step of assessing hydrogen environment severity, based on a measurement result in the measurement step.

In the assessment step, an increase rate of the amount of room temperature non-diffusible hydrogen contained in a rolling fatigue region of the steel rolling member during operation of the rolling device is calculated based on the amount of room temperature non-diffusible hydrogen measured in the measurement step and hydrogen environment severity can be assessed based on the calculation result.

Although, as described afore, room temperature diffusible hydrogen easily diffuses at room temperature and it is difficult to measure an accurate content of room temperature diffusible hydrogen, using the "increase rate of the amount of room temperature non-diffusible hydrogen" as a substitute index for the content of room temperature diffusible hydrogen enables the hydrogen environment severity (such as, hydrogen gas concentration in an atmosphere and likelihood of hydrogen being generated due to decomposition of a lubricant, such as lubricating oil) to be assessed.

The amount of room temperature non-diffusible hydrogen contained in a rolling fatigue region of a steel rolling member is measured before and after operation of the rolling device, the amount of room temperature non-diffusible hydrogen that has increased during operation of the rolling device is acquired, and an increase rate of room temperature non-diffusible hydrogen is calculated. By using the increase rate of room temperature non-diffusible hydrogen, it is possible to assess the hydrogen environment severity of the rolling device during operation. It is also possible to assess even hydrogen environment severity of a rolling device in an actual machine during operation, which is generally difficult to assess. Further, it is possible to assess hydrogen environment severity even at a stage at which white structure or white structure damage has not occurred to the steel rolling members.

The assessment of hydrogen environment severity may be performed quantitatively or qualitatively. Examples of the quantitative assessment of hydrogen environment severity include calculation of an index representing hydrogen environment severity. Examples of the qualitative assessment of hydrogen environment severity include acquiring the degree of severity of hydrogen environment "assessed as good or bad", "assessed in a plurality of levels, such as A, B, C, and D", and "assessed in comparison with a predetermined criterion value". Examples of the criterion value serving as a comparison target include hydrogen environment severity of another sample and hydrogen environment severity serving as a critical value for determining whether or not white structure damage occurs.

When the amount of room temperature non-diffusible hydrogen is measured, the amount of room temperature non-diffusible hydrogen contained in a rolling fatigue region that is a part where rolling fatigue has been produced by rolling contact within a steel rolling member of the rolling device after operation (the amount is referred to as a "measured value after operation") is measured. As a specific example, a portion directly beneath a part coming into rolling contact with another rolling member within the steel rolling member (for example, when the rolling device is a rolling bearing, a raceway surface in a load zone of the raceway ring) is cut out and the content of room temperature non-diffusible hydrogen is measured.

In addition, the amount of room temperature non-diffusible hydrogen contained in a region that becomes a rolling fatigue region during operation within the steel rolling member of the rolling device before operation is measured, or a portion directly beneath a part where rolling fatigue has not occurred within the steel rolling member of the rolling device after operation (for example, when the rolling device is a rolling bearing, a raceway surface in a non-load zone of the raceway ring) is cut out and the content of room temperature non-diffusible hydrogen is measured (this content is referred to as "measured value before operation"). By subtracting the amount of room temperature non-diffusible hydrogen that had been contained in the steel rolling member before operation (for example, hydrogen absorbed in heat treatment) through subtraction of the measured value before operation from the measured value after operation, an increased amount of room temperature non-diffusible hydrogen during operation is calculated. Further, by dividing the calculated increased amount of room temperature non-diffusible hydrogen by the number of repetitions of stress or operating time, an increase rate of the amount of room temperature non-diffusible hydrogen during operation is calculated. Based on the calculated increase rate of the amount of room temperature non-diffusible hydrogen, it is possible to assess the hydrogen environment severity.

Since, by using a thermal desorption analyzer, it is possible to heat a steel rolling member while increasing the temperature thereof, it is possible to cause room temperature diffusible hydrogen and room temperature non-diffusible hydrogen within the steel rolling member to be discharged separately and individually measure the amount of room temperature diffusible hydrogen and the amount of room temperature non-diffusible hydrogen. Since the amount of room temperature non-diffusible hydrogen sometimes has some peaks, the precision of measurement may be increased by performing peak separation and selecting a peak having significant influence.

In the measurement step, the amount of room temperature non-diffusible hydrogen may be measured after room temperature diffusible hydrogen has been discharged from the steel rolling member by maintaining the temperature of the steel rolling member at 100° C. or lower, in both measurements of a measured value after operation and a measured value before operation. Since performing this processing causes room temperature diffusible hydrogen to be securely discharged from the steel rolling member, it is possible to measure the amount of room temperature non-diffusible hydrogen more accurately. In addition, performing the afore-described maintenance of the temperature of the steel rolling member at 100° C. or lower enables only room temperature non-diffusible hydrogen to be easily measured without using a thermal desorption analyzer.

Although the temperature at which the steel rolling member is maintained is not specifically limited as long as the temperature is 100° C. or lower, the temperature is more preferably 80° C. or lower in order to suppress discharge of room temperature non-diffusible hydrogen and measure the amount of room temperature non-diffusible hydrogen more accurately. In addition, although the temperature at which the steel rolling member is maintained is not specifically limited as long as the temperature is higher than room temperature, the temperature is more preferably 35° C. or higher in order to cause room temperature diffusible hydrogen to be surely discharged and measure the amount of room temperature non-diffusible hydrogen more accurately.

Further, in the measurement step, the above-described measurement may be performed after hydrogen charge has been artificially performed on the steel rolling member serving as a measurement sample and a measured value of the measurement may be used as the above-described "measured value after operation". Even when the temperature of the steel rolling member serving as a measurement sample has increased and a portion or all of room temperature non-diffusible hydrogen has been discharged before measurement of the amount of room temperature non-diffusible hydrogen in the measurement step is performed, performing the hydrogen charge before the measurement enables hydrogen to be trapped again in trapping sites generated during the rolling fatigue process. This method enables the amount of room temperature non-diffusible hydrogen to be measured more accurately.

As described above, it is possible to assess hydrogen environment severity, based on a calculated increase rate of the amount of room temperature non-diffusible hydrogen. When all of the operating conditions (the magnitude of stress, the number of repetitions of stress, temperature, and the like) for rolling devices, the types of the rolling devices, and the types of steel that forms the steel rolling members of the rolling devices are identical to each other, comparing numerical values of the increase rates of the amounts of room temperature non-diffusible hydrogen enables hydrogen environment severity of a rolling device during operation to be assessed. In other words, it is possible to use a numerical value of the increase rate of the amount of room temperature non-diffusible hydrogen as an index representing hydrogen environment severity.

For example, in the case of comparing hydrogen environment severity values of a plurality of rolling devices during operation, when all of the operating conditions for the plurality of rolling devices, the types of the rolling devices, and the types of steel that forms the steel rolling members are identical to each other, comparing calculated numerical values of the increase rates of the amounts of room temperature non-diffusible hydrogen enables order of hydrogen environment severity values of the plurality of rolling devices during operation to be determined or a difference between degrees of hydrogen environment severity to be calculated.

When a database storing increase rates of the amount of room temperature non-diffusible hydrogen in a rolling device operated in various operating conditions (a hydrogen environment, the magnitude of stress, the number of repetitions of stress, temperature, and the like) is retained, comparing an increase rate of the amount of room temperature non-diffusible hydrogen in a rolling device the hydrogen environment severity of which is to be assessed and increase rates of the amount of room temperature non-diffusible hydrogen in the rolling device stored in the database with each other enables hydrogen environment severity of the rolling device the hydrogen environment severity of which is to be assessed to be easily assessed.

A hydrogen environment severity assessment method using the database will be described below in detail. First, rolling devices of the same type (all of a type, a shape, a dimension, a material (the type of steel forming steel rolling members), and the like are the same) as a rolling device the hydrogen environment severity of which is to be assessed are prepared as rolling devices for database generation. A rolling device for database generation is operated under each of a plurality of operating conditions in each of which at least one of the magnitude and the number of repetitions of stress exerted on a rolling fatigue region of a steel rolling member due to rolling contact, temperature during operation, and a hydrogen environment of the rolling device for database generation during operation is different from the other conditions.

Every time the operation of the rolling device for database generation is finished, the amount of room temperature non-diffusible hydrogen contained in a rolling fatigue region of a steel rolling member of the rolling device for database generation is measured and an increase rate of the amount of room temperature non-diffusible hydrogen contained in the rolling fatigue region of the steel rolling member of the rolling device for database generation is calculated. A database in which results of the calculation classified for each of the plurality of operating conditions are stored is generated.

Since the database preferably stores as many calculation results as possible, it is preferable to generate a database by not only performing operation under a large number of operating conditions and acquiring a large number of calculation results with respect to a type of rolling device but also acquiring calculation results with respect to as many types of rolling devices as possible. In other words, it is preferable to perform operation under a large number of operating conditions with respect to a large number of types of rolling devices for each of which at least one of a type, a shape, a dimension, and a material (the type of steel forming the steel rolling member) is different from the other rolling devices, acquire a large number of calculation results, and generate a database in which the calculation results classified for each of the conditions are stored.

Next, with respect to the rolling device the hydrogen environment severity of which is to be assessed, the amount of room temperature non-diffusible hydrogen contained in a rolling fatigue region of the steel rolling member is measured after operation of the rolling device and an increase rate of the amount of room temperature non-diffusible hydrogen is calculated. In addition, the operating conditions for the rolling device the hydrogen environment severity of which is to be assessed are confirmed. In other words, the magnitude and the number of repetitions of stress exerted on the rolling fatigue region of the steel rolling member due to rolling contact and temperature during operation are confirmed.

The database, which has been generated in advance, is searched, and data in the case where all of the magnitude and the number of repetitions of stress exerted on the rolling fatigue region of the steel rolling member due to rolling contact and temperature during operation are the same as the operating conditions for the rolling device the hydrogen environment severity of which is to be assessed (hereinafter, referred to as "data in the case where all the operating conditions are the same") are extracted. In other words, a calculation result of the increase rate of the amount of room temperature non-diffusible hydrogen contained in the rolling fatigue region of the steel rolling member is acquired.

When, as a result of the search of the database, no "data in the case where all the operating conditions are the same" exists, a plurality of arbitrary pieces of data are extracted and the above-described "data in the case where all the operating conditions are the same" are estimated based on the extracted data, using a method such as linear interpolation.

As the plurality of pieces of data extracted from the database, for example, data in the case where some of the magnitude and the number of repetitions of stress exerted on the rolling fatigue region of the steel rolling member due to rolling contact and temperature during operation are the same as the operating conditions for the rolling device the hydrogen environment severity of which is to be assessed and the others are different or data in the case where all the conditions are close to the operating conditions for the rolling device the hydrogen environment severity of which is to be assessed can be extracted. Hereinafter, a calculation result of the increase rate of the amount of room temperature non-diffusible hydrogen that is acquired from the database or estimated from data in the database is sometimes referred to as "database value".

Since, in the database, a plurality of calculation results for cases the hydrogen environments of which are different from one another in a variety of manners are stored, such a plurality of calculation results are acquired. The plurality of calculation results acquired from the database and a calculation result of the increase rate of the amount of room temperature non-diffusible hydrogen calculated with respect to the rolling device the hydrogen environment severity of which is to be assessed are compared with each other.

When, as a result of the comparison, a database value the numerical value of which coincides with the calculation result with respect to the rolling device the hydrogen environment severity of which is to be assessed exists among the plurality of database values, the database is searched and the hydrogen environment of the rolling device for database generation for which the coincident database value was calculated is confirmed. For example, hydrogen gas concentration in an atmosphere around the rolling device for database generation for which the coincident database value was calculated and the type of lubricant used in the rolling device for database generation are confirmed.

Based on the hydrogen environment of the rolling device for database generation for which the coincident database value was calculated, hydrogen environment severity of the rolling device the hydrogen environment severity of which is to be assessed is assessed. For example, since it can be determined that the hydrogen environment severity of the rolling device the hydrogen environment severity of which is to be assessed is the same as the hydrogen environment severity of the rolling device for database generation for which the coincident database value was calculated, it can also be determined that the hydrogen gas concentration in an atmosphere around the rolling device and the type of lubricant used in the rolling device are the same. Thus, the hydrogen gas concentration in the atmosphere around the rolling device for database generation for which the coincident database value was calculated and the type of lubricant used can be assessed as hydrogen environment severity of the rolling device the hydrogen environment severity of which is to be assessed.

Note that, when no database value the numerical value of which coincides with the calculation result with respect to the rolling device the hydrogen environment severity of which is to be assessed exists among the plurality of database values, hydrogen environment severity of the rolling device the hydrogen environment severity of which is to be assessed can be assessed using a method of performing linear interpolation based on the above-described plurality of database values or the like.

As described in the foregoing, use of the hydrogen environment severity assessment method of the present embodiment enables hydrogen environment severity to be easily assessed using the above-described database even when, for example, the hydrogen environment severity of a rolling device used in an actual machine is unknown. The hydrogen environment severity assessment method of the present embodiment can also be used for assessing likelihood of hydrogen being generated due to decomposition of a lubricant.

As described above, when all of the operating conditions (the magnitude of stress, the number of repetitions of stress, temperature, and the like) for rolling devices, the types of the rolling devices, and the types of steel that forms steel rolling members of the rolling devices are identical to each other, comparing numerical values of the increase rates of the amounts of room temperature non-diffusible hydrogen enables the hydrogen environment severity of a rolling device during operation to be assessed.

However, when at least one of the operating conditions for rolling devices, the types of the rolling devices, and the types of steel that forms steel rolling members of the rolling devices are different from each other, the increase rates of the amounts of room temperature non-diffusible hydrogen cannot be directly compared with each other. Thus, when at least one of the operating conditions for rolling devices are different from each other, hydrogen environment severity can be calculated using the formulae below.

Regarding hydrogen environment severity calculated using the formulae below, when the types of rolling devices and the types of steel that forms steel rolling members of the rolling devices are identical to each other, calculated numerical values of hydrogen environment severity can be directly compared with each other even when the operating conditions for the rolling devices are different from each other. In other words, the formulae below are formulae that quantify the increase rate of the amount of room temperature non-diffusible hydrogen by correcting the increase rate with the conditions of the magnitude of stress and the number of repetitions of stress.

The formulae will be described below. Since, as described afore, hydrogen environment severity can be expressed by a function of the amount of rolling fatigue hydrogen, the number of repetitions of stress, and surface pressure, the hydrogen environment severity can, for example, be expressed by the following formulae:

[hydrogen environment severity]=$A$×[the magnitude of stress (surface pressure)]$^\alpha$+$B$×[the number of repetitions of stress]$^\beta$+$C$×[the amount of rolling fatigue hydrogen (an increased amount of room temperature non-diffusible hydrogen)]$^\gamma$;

[the amount of rolling fatigue hydrogen (an increased amount of room temperature non-diffusible hydrogen)]=($D$×[hydrogen environment severity]+$E$×[the magnitude of stress (surface pressure or the like)])×[the number of repetitions of stress]+$F$; and

[the amount of rolling fatigue hydrogen (an increased amount of room temperature non-diffusible hydrogen)]=$G$×[the number of repetitions of stress]^($H$×[hydrogen environment severity]+$I$×[the magnitude of stress (surface pressure or the like)]).

Obtaining coefficients A to I, $\alpha$, $\beta$, and $\gamma$ in the above-described formulae by accumulating a large amount of data and generating a regression equation based on the data enables the above-described formulae to be completed. The completion of the formulae and substituting a measured value of the increased amount of room temperature non-diffusible hydrogen and the magnitude and the number of repetitions of stress, which are operating conditions for a rolling device, into the above-described formulae enable an index representing hydrogen environment severity to be calculated. This index enables hydrogen environment severity of the rolling device during operation to be evaluated, and, even when operating conditions for a plurality of rolling devices are different from each other, directly comparing the indices with each other with respect to the rolling devices enables hydrogen environment severity values of the respective rolling devices during operation to be compared with each other.

Next, a white structure damage likelihood prediction method for predicting likelihood that white structure damage occurs to steel rolling members during operation of a rolling device will be described. By use of the hydrogen environment severity assessment method of the present embodiment, it is possible to predict white structure damage likelihood of a rolling device easily and quantitatively.

First, a database that is similar to the above-described database, which is used for assessing hydrogen environment severity, is generated. However, although the above-described database, which is used for assessing hydrogen environment severity, is a database in which calculation results of the increase rate of the amount of room temperature non-diffusible hydrogen contained in a rolling fatigue region of a steel rolling member are classified for each of a plurality of operating conditions and stored, the database used for predicting white structure damage likelihood is a database in which calculation results of the increase rate of the amount of room temperature non-diffusible hydrogen contained in a rolling fatigue region of a steel rolling member and confirmation results from confirming whether or not white structure damage has occurred to the steel rolling member are classified for each of a plurality of operating conditions and stored.

In other words, a rolling device of the same type (all of a type, a shape, a dimension, a material (the type of steel forming steel rolling members), and the like are the same) as the rolling device for which likelihood that white structure damage occurs is to be predicted is prepared as a rolling device for database generation. The rolling device for database generation is operated under each of a plurality of operating conditions in each of which at least one of the magnitude and the number of repetitions of stress exerted on a rolling fatigue region of a steel rolling member due to rolling contact, temperature during operation, and a hydrogen environment of the rolling device for database generation during operation is different from the other conditions.

Every time the operation of the rolling device for database generation is finished, the amount of room temperature non-diffusible hydrogen contained in a rolling fatigue region of a steel rolling member of the rolling device for database generation is measured and an increase rate of the amount of room temperature non-diffusible hydrogen contained in the rolling fatigue region of the steel rolling member of the rolling device for database generation is calculated. In addition, whether or not white structure damage has occurred to the steel rolling member of the rolling device for database generation is confirmed. A database in which results of the calculation and results of the confirmation classified for each of the plurality of operating conditions are stored is generated.

Since the database preferably stores as many calculation results as possible, it is preferable to generate a database by not only performing operation under a large number of operating conditions and acquiring a large number of calculation results and confirmation results with respect to a type of rolling device but also acquiring calculation results and confirmation results with respect to as many types of rolling devices as possible. In other words, it is preferable to perform operation under a large number of operating conditions with respect to a large number of types of rolling devices for each of which at least one of a type, a shape, a dimension, and a material (the type of steel forming the steel rolling member) is different from the other rolling devices, acquire a large number of calculation results and confirmation results, and generate a database in which the calculation results and the confirmation results classified for each of the conditions are stored.

Next, with respect to the rolling device for which likelihood that white structure damage occurs is to be predicted, the amount of room temperature non-diffusible hydrogen contained in a rolling fatigue region of the steel rolling member is measured after operation of the rolling device and an increase rate of the amount of room temperature non-diffusible hydrogen is calculated. Whether or not white structure damage has occurred to the steel rolling member of the rolling device for which likelihood that white structure damage occurs is to be predicted may be confirmed or does not have to be confirmed. In addition, the operating conditions for the rolling device for which likelihood that white structure damage occurs is to be predicted are confirmed. In other words, the magnitude and the number of repetitions of stress exerted on the rolling fatigue region of the steel rolling member due to rolling contact and temperature during operation are confirmed.

The database, which has been generated in advance, is searched, and data in the case where all of the magnitude and the number of repetitions of stress exerted on the rolling fatigue region of the steel rolling member due to rolling contact and temperature during operation are the same as the operating conditions of the rolling device for which likelihood that white structure damage occurs is to be predicted (hereinafter, referred to as "data in the case where all the operating conditions are the same") are extracted. In other words, a calculation result of the increase rate of the amount of room temperature non-diffusible hydrogen contained in the rolling fatigue region of the steel rolling member and a confirmation result of whether or not white structure damage has occurred to the steel rolling member are acquired.

When, as a result of the search of the database, no "data in the case where all the operating conditions are the same" exists, a plurality of arbitrary pieces of data are extracted and the above-described "data in the case where all the operating conditions are the same" are estimated based on the extracted data, using a method such as linear interpolation, as with the afore-described case of the hydrogen environment severity assessment method.

Since, in the database, a plurality of calculation results and confirmation results for cases the hydrogen environments of which are different from one another in a variety of manners are stored, such a plurality of calculation results and confirmation results are acquired.

When calculation results and confirmation results are acquired from the database, an increase rate of the amount of room temperature non-diffusible hydrogen serving as a critical value at which white structure damage begins to occur is calculated using the acquired calculation results and confirmation results. The calculation result of the increase rate of the amount of room temperature non-diffusible hydrogen calculated with respect to the rolling device for which likelihood that white structure damage occurs is to be predicted and the above-described critical value are compared with each other. Based on a result of the comparison, it is possible to predict likelihood that white structure damage occurs to the steel rolling members during operation of the rolling device for which likelihood that white structure damage occurs is to be predicted.

For example, when the calculation result of the increase rate of the amount of room temperature non-diffusible hydrogen calculated with respect to the rolling device for which likelihood that white structure damage occurs is to be predicted is greater than the critical value, it is possible to predict that the rolling device for which likelihood that white structure damage occurs is to be predicted has high likelihood that white structure damage occurs.

On the other hand, when the calculation result of the increase rate of the amount of room temperature non-diffusible hydrogen calculated with respect to the rolling device for which likelihood that white structure damage occurs is to be predicted is smaller than the critical value, it is possible to predict that the rolling device for which likelihood that white structure damage occurs is to be predicted has low likelihood that white structure damage occurs.

In addition, when the calculation result of the increase rate of the amount of room temperature non-diffusible hydrogen calculated with respect to the rolling device for which likelihood that white structure damage occurs is to be predicted is greater than the critical value and as a difference between the calculation result and the critical value becomes larger, it is possible to predict that the likelihood that white structure damage occurs becomes higher, and, when the calculation result is smaller than the critical value and as a difference therebetween becomes larger, it is possible to predict that the likelihood that white structure damage occurs becomes lower.

Further, when a database value the numerical value of which coincides with the calculation result of the increase rate of the amount of room temperature non-diffusible hydrogen calculated with respect to the rolling device for which likelihood that white structure damage occurs is to be predicted exists among a plurality of database values acquired from the database, it is possible to predict that white structure damage likelihood of the rolling device for which likelihood that white structure damage occurs is to be predicted is equal to that of a rolling device for database generation for which the coincident database value is calculated. Thus, based on a life of the rolling device for database generation for which the coincident database value is calculated, it is also possible to predict a life of the rolling device for which likelihood that white structure damage occurs is to be predicted.

An example of a calculation method of a critical value will be described using FIG. 3. In the example in FIG. 3, different hydrogen environments are set by changing the type of lubricating oil used for the rolling device for database generation into a variety of types.

First, rolling life tests (equivalent to operation of the rolling device for database generation) that were performed to generate the graph in FIG. 3 will be described. The rolling life tests were performed using six types of lubricating oil A to F for deep-groove ball bearings each of which has bearing designation 6206, the inner ring and outer ring of each of which are made of SUJ2, and the balls of each of which are made of SUJ2 on which carbonitriding treatment was performed (equivalent to the rolling device for database generation). Test conditions are as follows: a ratio of dynamic equivalent load P to basic dynamic load rating C is 0.46; rotational speed is 3000 $min^{-1}$; and temperature is 110° C.

Every time a rolling life test was performed for a predetermined period of time, the amount of room temperature non-diffusible hydrogen contained in a rolling fatigue region of a raceway ring (the inner ring or the outer ring) was measured, and an increase rate of the amount of room temperature non-diffusible hydrogen contained in the rolling fatigue region was calculated and, in conjunction therewith, whether or not white structure damage had occurred to the rolling fatigue region of the raceway ring was confirmed. Using the calculation results and the confirmation results, the graph in FIG. 3 was generated (equivalent to generation of a database).

Note that the amount of room temperature non-diffusible hydrogen contained in the rolling fatigue region was measured by heating the raceway ring in a vacuum, using the thermal desorption analyzer EMD-WA1000S produced by ESCO, Ltd and thereby detaching room temperature non-diffusible hydrogen and detecting the detached hydrogen, using a quadrupole mass spectrometer. The amount of room temperature non-diffusible hydrogen of the raceway ring after a rolling life test and the amount of room temperature non-diffusible hydrogen of an unused raceway ring were measured and, based on the measured amounts, an increased amount of room temperature non-diffusible hydrogen during operation was calculated. Whether or not white structure damage had occurred was determined by performing cross-sectional structure observation of a portion directly beneath the raceway surface of the raceway ring.

Figure 3:
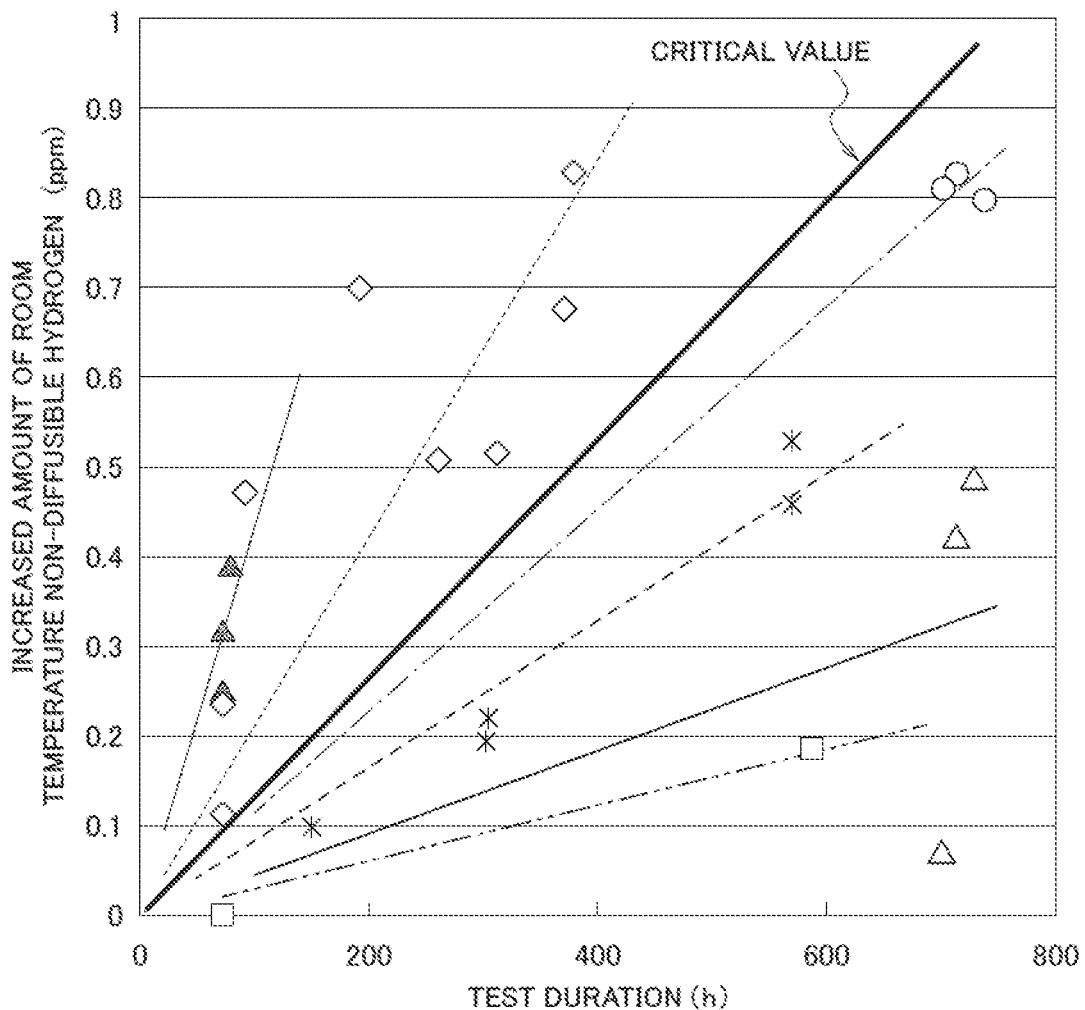
FIG. 3 is a graph descriptive of a white structure damage likelihood prediction method.

The graph illustrated in FIG. 3 is a graph illustrated by plotting increased amounts of room temperature non-diffusible hydrogen at respective test durations on a graph the abscissa and the ordinate of which represent the test duration and the increased amount of room temperature non-diffusible hydrogen, respectively, and, in addition thereto, calculating and drawing a regression line with respect to each set of plots the hydrogen environment conditions of which are identical to one another, using a least-square method. Each of the regression lines is equivalent to an increase rate of the amount of room temperature non-diffusible hydrogen. The increased amounts of room temperature non-diffusible hydrogen may be calculated from calculation results of the increase rate of the amount of room temperature non-diffusible hydrogen that are stored in the database and test durations (the numbers of repetitions of stress) every time likelihood that white structure damage occurs is predicted or may be stored in the database in advance.

When the plots representing calculation results on the graph are discriminated from one another based on confirmation results of whether or not white structure damage occurred (equivalent to confirmation results acquired from the database), the graph can be divided into an area in which regression lines drawn from plots relating to deep-groove ball bearings (rolling devices for database generation) in which white structure flaking occurred are arranged and an area in which regression lines drawn only from plots relating to deep-groove ball bearings (rolling devices for database generation) in which white structure flaking did not occur are arranged. As illustrated in FIG. 3, a straight line can be drawn at the boundary between the two areas (equivalent to calculation of a critical value at which white structure damage begins to occur). An increase rate of the amount of room temperature non-diffusible hydrogen represented by the slope of the straight line serves as a critical value for whether or not white structure damage occurs.

Next, the calculation result of the increase rate of the amount of room temperature non-diffusible hydrogen calculated with respect to the rolling device for which likelihood that white structure damage occurs is to be predicted and the above-described critical value are compared with each other. It is possible to, based on a result of the comparison, predict likelihood that white structure damage occurs to the steel rolling member during operation of the rolling device for which likelihood that white structure damage occurs is to be predicted.

For example, when, in the graph in FIG. 3, the calculation result of the increase rate of the amount of room temperature non-diffusible hydrogen calculated with respect to the rolling device for which likelihood that white structure damage occurs is to be predicted is located in the area on the upper side of the critical value, that is, located in the area in which regression lines drawn from plots relating to deep-groove ball bearings in which white structure flaking occurred are arranged, it is possible to predict that the rolling device for which likelihood that white structure damage occurs is to be predicted has high likelihood that white structure damage occurs.

On the other hand, when the calculation result of the increase rate of the amount of room temperature non-diffusible hydrogen calculated with respect to the rolling device for which likelihood that white structure damage occurs is to be predicted is located in the area on the lower side of the critical value, that is, located in the area in which regression lines drawn only from plots relating to deep-groove ball bearings in which white structure flaking did not occur are arranged, it is possible to predict that the rolling device for which likelihood that white structure damage occurs is to be predicted has low likelihood that white structure damage occurs.

In addition, it is possible to predict that, the farther the calculation result of the increase rate of the amount of room temperature non-diffusible hydrogen calculated with respect to the rolling device for which likelihood that white structure damage occurs is to be predicted is separated upward from the critical value, the higher the likelihood that white structure damage occurs is, and it is possible to predict that, the farther the calculation result is separated downward from the critical value, the lower the likelihood that white structure damage occurs is.

As described in the foregoing, use of the white structure damage likelihood prediction method of the present embodiment enables the white structure damage likelihood to be easily and quantitatively assessed using the above-described database even when the hydrogen environment severity of a rolling device used in an actual machine is unknown. The white structure damage likelihood prediction method of the present embodiment can also be used for assessing likelihood of hydrogen being generated due to decomposition of lubricant.

As described above, when all of the operating conditions (the magnitude of stress, the number of repetitions of stress, temperature, and the like) of rolling devices, the types of the rolling devices, and the types of steel that forms steel rolling members of the rolling devices are identical, comparing numerical values of the increase rates of the amounts of room temperature non-diffusible hydrogen enables the white structure damage likelihood of a rolling device during operation to be assessed.

It should be noted that the foregoing embodiment is one example of the present invention and the present invention is not limited to the foregoing embodiment. In addition, various modifications and improvements may be made to the present embodiment, and the embodiment to which such modifications and improvements are made may be included in the present invention. Further, although the present invention is a hydrogen environment severity assessment method and a white structure damage likelihood prediction method relating to a rolling device, the present invention is applicable to, without being limited to a rolling device, two rolling members that come into rolling contact with each other.

The invention claimed is:

1. A hydrogen environment severity assessment method for assessing, among operating conditions for a rolling device including two rolling members coming into rolling contact with each other and having at least one of the two rolling members being a steel rolling member, hydrogen environment severity, the hydrogen environment severity being an index representing magnitude of influence exerted by hydrogen, the method comprising:
a measurement step of measuring the amount of room temperature non-diffusible hydrogen contained in a rolling fatigue region, the rolling fatigue region being a region where rolling fatigue has been produced by rolling contact, within the steel rolling member of the rolling device operated under the operating conditions; and
an assessment step of assessing the hydrogen environment severity, based on a measurement result in the measurement step, wherein
in the assessment step, the method calculates an increase rate of the amount of room temperature non-diffusible hydrogen contained in a rolling fatigue region of the steel rolling member during operation of the rolling device, based on the amount of the room temperature non-diffusible hydrogen measured in the measurement step and assesses the hydrogen environment severity, based on the calculation result,
in the measurement step, the method causes room temperature diffusible hydrogen to be discharged from the steel rolling member by maintaining temperature of the steel rolling member at 100° C. or lower and subsequently measure the amount of room temperature non-diffusible hydrogen contained in the rolling fatigue region wherein the method prepares a rolling device of a same type as a rolling device the hydrogen environment severity of which is to be assessed as a rolling device for database generation, operates the rolling device for database generation under each of a plurality of operating conditions in each of which at least one of the magnitude and the number of repetitions of stress exerted on a rolling fatigue region of a steel rolling member due to rolling contact, temperature during operation, and a hydrogen environment of the rolling device for database generation during operation is different from the other conditions, measures the amount of room temperature non-diffusible hydrogen contained in the rolling fatigue region of the steel rolling member of the rolling device for database generation and calculates an increase rate of the amount of room temperature non-diffusible hydrogen contained in the rolling fatigue region of the steel rolling member of the rolling device for database generation every time the operation is finished, and generates a database in which the calculation results classified for each of the plurality of operating conditions are stored in advance,
the method acquires or estimates the calculation result in a case where all of the magnitude and the number of repetitions of stress exerted on a rolling fatigue region of a steel rolling member due to rolling contact and temperature during operation are same as operating conditions of a rolling device the hydrogen environment severity of which is to be assessed, from the database,
in the assessment step, the method compares a calculation result of an increase rate of the amount of room temperature non-diffusible hydrogen calculated with respect to the rolling device the hydrogen environment severity of which is to be assessed with the calculation result acquired or estimated from the database, and
based on a hydrogen environment of a rolling device for database generation the calculation result of which coincides with a calculation result with respect to the rolling device the hydrogen environment severity of which is to be assessed, the method assesses hydrogen environment severity of the rolling device the hydrogen environment severity of which is to be assessed.

2. A white structure damage likelihood prediction method for, using the hydrogen environment severity assessment method according to claim 1, predicting likelihood that white structure damage occurs to the steel rolling member during operation of a rolling device, wherein
the method prepares a rolling device of a same type as a rolling device for which likelihood that white structure damage occurs is to be predicted as a rolling device for database generation, operates the rolling device for database generation under each of a plurality of operating conditions in each of which at least one of the magnitude and the number of repetitions of stress exerted on a rolling fatigue region of a steel rolling member due to rolling contact, temperature during operation, and a hydrogen environment of the rolling device for database generation during operation is different from the other conditions, measures the amount of room temperature non-diffusible hydrogen contained in the rolling fatigue region of the steel rolling member of the rolling device for database generation and calculates an increase rate of the amount of room temperature non-diffusible hydrogen contained in the rolling fatigue region of the steel rolling member of the rolling device for database generation and simultaneously confirms whether or not white structure damage has occurred to the steel rolling member of the rolling device for database generation every time the operation is finished, and generates a database in which the calculation results and confirmation results classified for each of the plurality of operating conditions are stored in advance,
the method acquires or estimates the calculation result and the confirmation result in a case where all of the magnitude and the number of repetitions of stress exerted on a rolling fatigue region of a steel rolling member due to rolling contact and temperature during operation are same as operating conditions of a rolling device for which likelihood that the white structure damage occurs is to be predicted, from the database and, using the acquired or estimated calculation result and confirmation result, calculates an increase rate of the amount of room temperature non-diffusible hydrogen serving as a critical value at which the white structure damage begins to occur, and in the assessment step, by comparing an increase rate of the amount of room temperature non-diffusible hydrogen calculated with respect to a rolling device for which likelihood that the white structure damage occurs is to be predicted with the critical value, the method predicts likelihood that white structure damage occurs to the steel rolling member during operation of a rolling device for which likelihood that the white structure damage occurs is to be predicted.

3. A hydrogen environment severity assessment method for assessing, among operating conditions for a rolling device including two rolling members coming into rolling contact with each other and having at least one of the two rolling members being a steel rolling member, hydrogen environment severity, the hydrogen environment severity being an index representing magnitude of influence exerted by hydrogen, the method comprising:

a measurement step of measuring an amount of room temperature non-diffusible hydrogen contained in a rolling fatigue region, the rolling fatigue region being a region where rolling fatigue has been produced by rolling contact, within the steel rolling member of the rolling device operated under the operating conditions; and an assessment step of assessing the hydrogen environment severity, based on a measurement result in the measurement step, wherein in the assessment step, the method calculates an increase rate of the amount of room temperature non-diffusible hydrogen contained in the rolling fatigue region of the steel rolling member during operation of the rolling device, based on the amount of the room temperature non-diffusible hydrogen measured in the measurement step and assesses the hydrogen environment severity, based on a calculation result.

4. The hydrogen environment severity assessment method according to claim 3, wherein the method prepares a rolling device of a same type as a rolling device the hydrogen environment severity of which is to be assessed as a rolling device for database generation, operates the rolling device for database generation under each of a plurality of operating conditions in each of which at least one of the magnitude and the number of repetitions of stress exerted on a rolling fatigue region of a steel rolling member due to rolling contact, temperature during operation, and a hydrogen environment of the rolling device for database generation during operation is different from the other conditions, measures the amount of room temperature non-diffusible hydrogen contained in the rolling fatigue region of the steel rolling member of the rolling device for database generation and calculates an increase rate of the amount of room temperature non-diffusible hydrogen contained in the rolling fatigue region of the steel rolling member of the rolling device for database generation every time the operation is finished, and generates a database in which the calculation results classified for each of the plurality of operating conditions are stored in advance, the method acquires or estimates the calculation result in a case where all of the magnitude and the number of repetitions of stress exerted on a rolling fatigue region of a steel rolling member due to rolling contact and temperature during operation are same as operating conditions of a rolling device the hydrogen environment severity of which is to be assessed, from the database, in the assessment step, the method compares a calculation result of an increase rate of the amount of room temperature non-diffusible hydrogen calculated with respect to the rolling device the hydrogen environment severity of which is to be assessed with the calculation result acquired or estimated from the database, and based on a hydrogen environment of a rolling device for database generation the calculation result of which coincides with a calculation result with respect to the rolling device the hydrogen environment severity of which is to be assessed, the method assesses hydrogen environment severity of the rolling device the hydrogen environment severity of which is to be assessed.

5. The hydrogen environment severity assessment method according to claim 3, wherein in the measurement step, the method causes room temperature diffusible hydrogen to be discharged from the steel rolling member by maintaining temperature of the steel rolling member at 100° C. or lower and subsequently measure the amount of room temperature non-diffusible hydrogen contained in the rolling fatigue region.

6. A white structure damage likelihood prediction method for, using the hydrogen environment severity assessment method according to claim 3, predicting likelihood that white structure damage occurs to the steel rolling member during operation of a rolling device, wherein the method prepares a rolling device of a same type as a rolling device for which likelihood that white structure damage occurs is to be predicted as a rolling device for database generation, operates the rolling device for database generation under each of a plurality of operating conditions in each of which at least one of the magnitude and the number of repetitions of stress exerted on a rolling fatigue region of a steel rolling member due to rolling contact, temperature during operation, and a hydrogen environment of the rolling device for database generation during operation is different from the other conditions, measures the amount of room temperature non-diffusible hydrogen contained in the rolling fatigue region of the steel rolling member of the rolling device for database generation and calculates an increase rate of the amount of room temperature non-diffusible hydrogen contained in the rolling fatigue region of the steel rolling member of the rolling device for database generation and simultaneously confirms whether or not white structure damage has occurred to the steel rolling member of the rolling device for database generation every time the operation is finished, and generates a database in which the calculation results and confirmation results classified for each of the plurality of operating conditions are stored in advance, the method acquires or estimates the calculation result and the confirmation result in a case where all of the magnitude and the number of repetitions of stress exerted on a rolling fatigue region of a steel rolling member due to rolling contact and temperature during operation are same as operating conditions of a rolling device for which likelihood that the white structure damage occurs is to be predicted, from the database and, using the acquired or estimated calculation result and confirmation result, calculates an increase rate of the amount of room temperature non-diffusible hydrogen serving as a critical value at which the white structure damage begins to occur, and in the assessment step, by comparing an increase rate of the amount of room temperature non-diffusible hydrogen calculated with respect to a rolling device for which likelihood that the white structure damage occurs is to be predicted with the critical value, the method predicts likelihood that white structure damage occurs to the steel rolling member during operation of a rolling device for which likelihood that the white structure damage occurs is to be predicted.

7. The hydrogen environment severity assessment method according to claim 6, wherein in the measurement step, the method causes room temperature diffusible hydrogen to be discharged from the steel rolling member by maintaining temperature of the steel rolling member at 100° C. or lower and subsequently measure the amount of room temperature non-diffusible hydrogen contained in the rolling fatigue region.

8. A hydrogen environment severity assessment method for assessing, among operating conditions for a rolling device including two rolling members coming into rolling contact with each other and having at least one of the two rolling members being a steel rolling member, hydrogen environment severity, the hydrogen environment severity being an index representing magnitude of influence exerted by hydrogen, the method comprising:

a measurement step of measuring the amount of room temperature non-diffusible hydrogen contained in a rolling fatigue region, the rolling fatigue region being a region where rolling fatigue has been produced by rolling contact, within the steel rolling member of the rolling device operated under the operating conditions; and an assessment step of assessing the hydrogen environment severity, based on a measurement result in the measurement step, wherein in the measurement step, the method causes room temperature diffusible hydrogen to be discharged from the steel rolling member by maintaining temperature of the steel rolling member at 100° C. or lower and subsequently measure the amount of room temperature non-diffusible hydrogen contained in the rolling fatigue region.

9. The hydrogen environment severity assessment method of claim 8, wherein the method prepares a rolling device of a same type as a rolling device the hydrogen environment severity of which is to be assessed as a rolling device for database generation, operates the rolling device for database generation under each of a plurality of operating conditions in each of which at least one of the magnitude and the number of repetitions of stress exerted on a rolling fatigue region of a steel rolling member due to rolling contact, temperature during operation, and a hydrogen environment of the rolling device for database generation during operation is different from the other conditions, measures the amount of room temperature non-diffusible hydrogen contained in the rolling fatigue region of the steel rolling member of the rolling device for database generation and calculates an increase rate of the amount of room temperature non-diffusible hydrogen contained in the rolling fatigue region of the steel rolling member of the rolling device for database generation every time the operation is finished, and generates a database in which the calculation results classified for each of the plurality of operating conditions are stored in advance, the method acquires or estimates the calculation result in a case where all of the magnitude and the number of repetitions of stress exerted on a rolling fatigue region of a steel rolling member due to rolling contact and temperature during operation are same as operating conditions of a rolling device the hydrogen environment severity of which is to be assessed, from the database, in the assessment step, the method compares a calculation result of an increase rate of the amount of room temperature non-diffusible hydrogen calculated with respect to the rolling device the hydrogen environment severity of which is to be assessed with the calculation result acquired or estimated from the database, and based on a hydrogen environment of a rolling device for database generation the calculation result of which coincides with a calculation result with respect to the rolling device the hydrogen environment severity of which is to be assessed, the method assesses hydrogen environment severity of the rolling device the hydrogen environment severity of which is to be assessed.

10. A white structure damage likelihood prediction method for, using the hydrogen environment severity assessment method according to claim 8, predicting likelihood that white structure damage occurs to the steel rolling member during operation of a rolling device, wherein the method prepares a rolling device of a same type as a rolling device for which likelihood that white structure damage occurs is to be predicted as a rolling device for database generation, operates the rolling device for database generation under each of a plurality of operating conditions in each of which at least one of the magnitude and the number of repetitions of stress exerted on a rolling fatigue region of a steel rolling member due to rolling contact, temperature during operation, and a hydrogen environment of the rolling device for database generation during operation is different from the other conditions, measures the amount of room temperature non-diffusible hydrogen contained in the rolling fatigue region of the steel rolling member of the rolling device for database generation and calculates an increase rate of the amount of room temperature non-diffusible hydrogen contained in the rolling fatigue region of the steel rolling member of the rolling device for database generation and simultaneously confirms whether or not white structure damage has occurred to the steel rolling member of the rolling device for database generation every time the operation is finished, and generates a database in which the calculation results and confirmation results classified for each of the plurality of operating conditions are stored in advance, the method acquires or estimates the calculation result and the confirmation result in a case where all of the magnitude and the number of repetitions of stress exerted on a rolling fatigue region of a steel rolling member due to rolling contact and temperature during operation are same as operating conditions of a rolling device for which likelihood that the white structure damage occurs is to be predicted, from the database and, using the acquired or estimated calculation result and confirmation result, calculates an increase rate of the amount of room temperature non-diffusible hydrogen serving as a critical value at which the white structure damage begins to occur, and in the assessment step, by comparing an increase rate of the amount of room temperature non-diffusible hydrogen calculated with respect to a rolling device for which likelihood that the white structure damage occurs is to be predicted with the critical value, the method predicts likelihood that white structure damage occurs to the steel rolling member during operation of a rolling device for which likelihood that the white structure damage occurs is to be predicted.

\* \* \* \* \*